United States Patent
Coe et al.

(10) Patent No.: US 7,651,503 B1
(45) Date of Patent: Jan. 26, 2010

(54) ENDOCARDIAL LEAD CUTTING APPARATUS

(75) Inventors: Michael S. Coe, Plymouth, MN (US);
Duncan Sellers, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 938 days.

(21) Appl. No.: 11/259,477

(22) Filed: Oct. 26, 2005

(51) Int. Cl.
*A61B 17/32* (2006.01)
(52) U.S. Cl. .................... 606/108; 606/170; 607/122
(58) Field of Classification Search ............... None
See application file for complete search history.

(56) References Cited

U.S. PATENT DOCUMENTS

| | | | | |
|---|---|---|---|---|
| 4,988,347 A | * | 1/1991 | Goode et al. ............... 606/1 |
| 5,084,010 A | * | 1/1992 | Plaia et al. ................. 604/22 |
| 5,620,453 A | * | 4/1997 | Nallakrishnan ........... 606/166 |
| 2003/0065335 A1 | * | 4/2003 | Guido et al. .............. 606/144 |

* cited by examiner

*Primary Examiner*—Kennedy J Schaetzle
(74) *Attorney, Agent, or Firm*—Townsend and Townsend and Crew LLP

(57) ABSTRACT

The invention provides an apparatus for cutting an endocardial lead within a patient. The apparatus includes a tubular member and a tension member disposed therein. The tension member includes a distal end and a proximal end. A blade is affixed to the distal end of the tension member and an adjustment mechanism is adapted to adjust the tension member and blade between an extended position and a retracted position. The adjustment mechanism includes a female member, a male member and an anchor. The anchor is affixed to the proximal end of the tension member and the male member. Insertion and withdrawal of the male member within the female member moves the tension member and the blade between the extended position and the retracted position. An alternate embodiment includes a capture mechanism or guide wire for drawing the apparatus and lead closer together before extending the blade and cutting the lead.

30 Claims, 2 Drawing Sheets

ENDOCARDIAL LEAD CUTTING APPARATUS

FIELD OF THE INVENTION

This invention relates generally to an endocardial lead cutting apparatus and, more particularly, to an apparatus including at least one blade movable between an extended position and a retracted position for cutting endocardial leads from within a patient's body.

BACKGROUND OF THE INVENTION

In the past, various types of endocardial leads and electrodes have been introduced into different chambers of a patient's heart, including the right ventricle, right atrial appendage, and atrium as well as the coronary sinus. These flexible leads usually are composed of an insulator sleeve that contains an implanted helical coil conductor that is attached to an electrode tip. This electrode is placed in contact with myocardial tissue by passage through a venous access, often the subclavian vein or one of its tributaries, which leads to the endocardial surface of the heart chambers. The tip with the electrode contact is held in place by trabeculations of myocardial tissue.

The tips of many available leads include flexible tines, wedges, or finger-like projections which extend radially outward and usually are molded from and integral with the insulating sheath of the lead. These tines or protrusions allow surrounding growth of tissue in chronically implanted leads to fix the electrode tip in position in the heart and prevent dislodgement of the tip during the life of the lead. In "acute placement" of the electrode or lead tip, a blood clot forms about the flanges or tines (due to enzymes released as a result of irritation of the trabeculations of myocardial tissue by the presence of the electrode tip) until scar tissue eventually forms, usually in three to six months. The tines or wedges or finger-like projections allow better containment by the myocardial trabeculations of muscle tissue and prevent early dislodgement of the lead tip.

Although the state of the art in implemented pulse generator or pacemaker technology and endocardial lead technology has advanced considerably, endocardial leads nevertheless occasionally fail, due to a variety of reasons, including breakage of a lead, insulation breaks, breakage of the inner helical coil conductor and an increase in electrode resistance. Furthermore, in some instances, it may be desirable to electronically stimulate different portions of the heart than are presently being stimulated with the leads already implanted. There are a considerable number of patients who have one or more, and sometimes as many as four or five unused leads in their veins and heart.

Although it obviously would be desirable to easily remove such unused leads, in the past surgeons usually have avoided attempts to remove inoperative leads because the risk of removing them exceeded the risk of leaving them in. The risks of leaving unused myocardial leads in the heart and venous path include increased likelihood that an old lead may facilitate infection, which in turn may necessitate removal of the lead to prevent continued bacteremia and abcess formation. Furthermore, there is an increased likelihood of the formation of blood clots in the atrial chamber about entangled leads. Such clots may embolize to the lung and produce severe complications and even fatality. Furthermore, the presence of unused leads in the venous pathway and inside the heart can cause considerable difficulty in the positioning and attachment of new endocardial leads in the heart.

Removal of an inoperative lead sometimes can be accomplished by applying traction and rotation to the outer free end of the lead, but only if done prior to fixation of the lead tip in the trabeculations of myocardial tissue by scar tissue formation or large clot development. Even then, it is possible that a clot has formed so the removal of the leads causes various sized emboli to pass to the lungs, producing severe complications.

In cases where the lead tip has become attached by scar tissue to the myocardial wall, removal of the lead always has presented major problems and risks. Porous lead tips that are sometimes used may have an ingrowth of scar tissue attaching them to the myocardial wall. Sufficient traction on such leads in a removal attempt could cause disruption of the myocardial wall prior to release of the embedded lead tip. The tines or flanges of other types of leads that are not tightly scarred to the myocardial wall present similar risks. Even if screw-in tip electrodes are used, wherein the tips theoretically can be unscrewed from the myocardial wall, unscrewing of such tips may be prevented by a channel of scar tissue and endothelium that surrounds the outer surface of the lead along the venous pathway. Such "channel scar" tissue prevents withdrawal because of tight encasement of the lead. Continual strong pulling or twisting of the outer free end of the lead could cause rupture of the atrial wall or the ventricular wall if there is such tight circumferential encasement of adherent channel scar tissue in the venous path. Such tight encasement by scar tissue in the venous pathway and in the trabeculations of the myocardial wall typically occurs within six months to a year of the initial placement of the lead.

The risks of removing the lead by such traction and rotation of the lead are so high that, if it becomes imperative that the lead be removed (as in the case of infection), most surgeons have elected to open the patient's chest and surgically remove the lead rather than attempt removal by applying traction and rotation thereto.

Clearly, there is a need for an apparatus for extracting endocardial leads from a patient's heart with minimal risk to the patient.

SUMMARY OF THE INVENTION

To address these and other drawbacks, the present invention provides an apparatus for cutting the lead as near as possible to the lead's embedded electrode.

Specifically, the present invention provides an apparatus having a generally flexible tubular member and a tension member disposed therein. The tension member includes a distal end and a proximal end. A blade is affixed to the distal end of the tension member and an adjustment mechanism is adapted to adjust the tension member and blade between an extended position and a retracted position.

Other aspects of the invention will be apparent to those skilled in the art after reviewing the drawings and the detailed description below.

BRIEF DESCRIPTION OF THE DRAWINGS

The present invention will now be described, by way of example, with reference to the accompanying drawings, in which.

DETAILED DESCRIPTION

Figure 1:
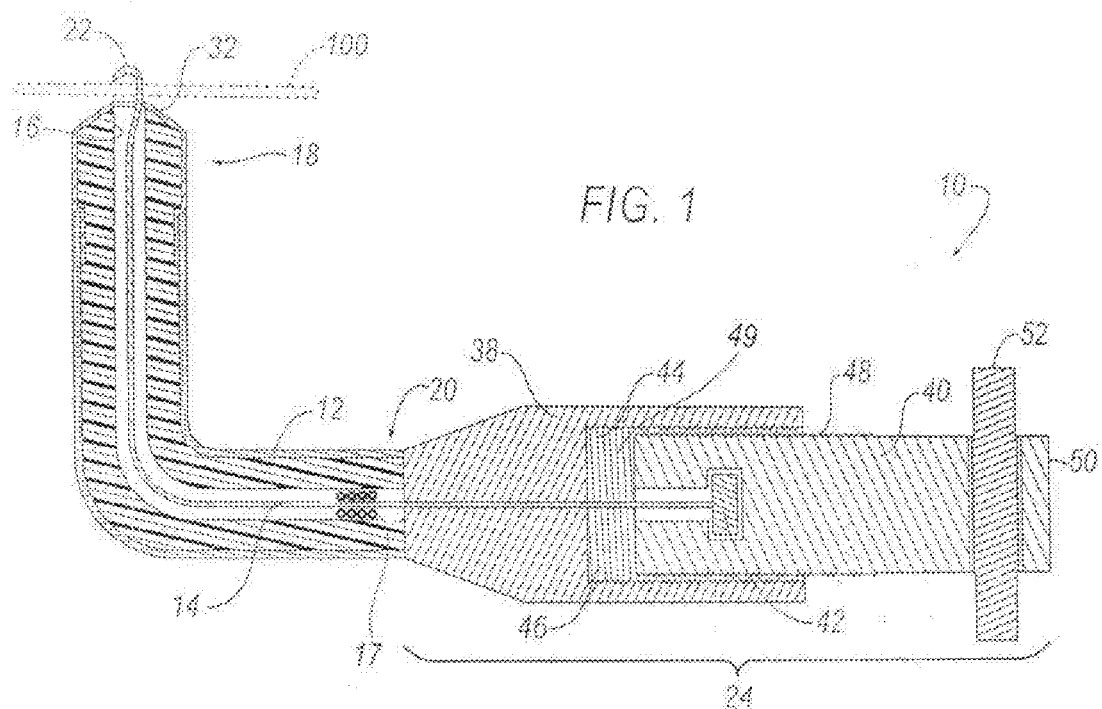
FIG. 1 illustrates a cross-sectional view of a first embodiment of an endocardial lead cutting apparatus of the present invention.
Figure 2:
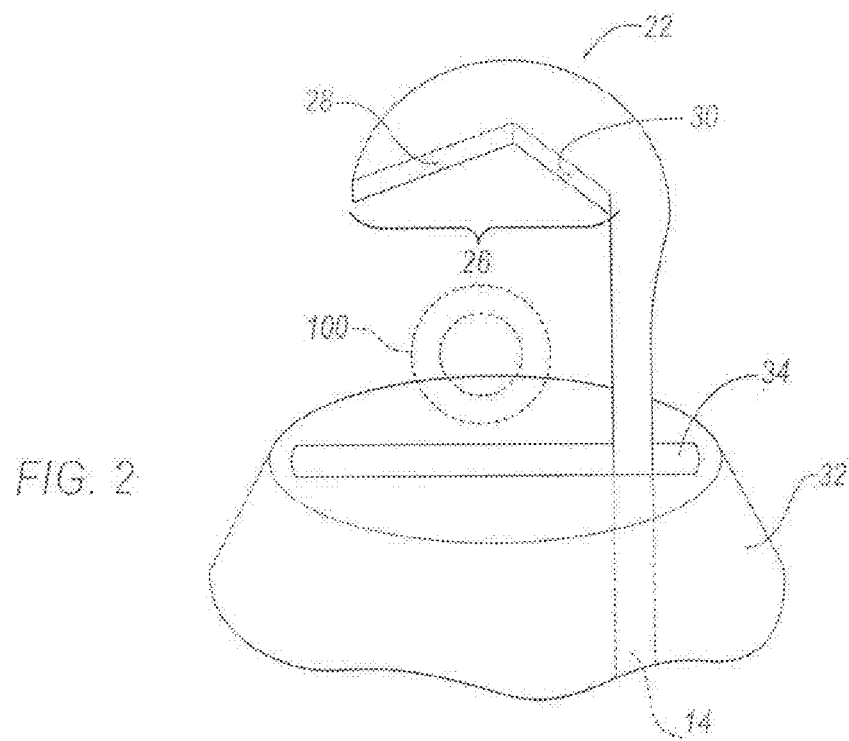
FIG. 2 illustrates an enlarged perspective view of a distal tip of the apparatus of the present invention.

Referring generally to FIGS. 1-3, embodiments of an endocardial lead cutting apparatus are generally referred to at 10.

Referring to FIG. 1, the apparatus 10 includes a tubular member 12. The tubular member 12 is generally flexible and preferably made from a polymer material. Additionally, the tubular member 12 is made from a generally radiopaque material such that the material does not allow the passage of x-rays or other forms of radiation. The tubular member 12 may include reinforcements such as a braid or compressed coil (not shown) to strengthen the tubular member 12 and resist compression during operation.

The apparatus 10 includes a tension member 14 disposed within the tubular member 12. The tension member 14 is received within a first channel 16 of the tubular member 12 and includes a distal end 18 and a proximal end 20. The tension member 14 is generally flexible and moveable between an extended position and a retracted position. Further, the first channel 16 may include a bearing surface 17, such as a coil, to facilitate movement between the positions. At least one blade 22 is affixed to the distal end 18 of the tension member 14. The apparatus 10 further includes an adjustment mechanism 24. The adjustment mechanism 24 adjusts the tension member 14 and, accordingly, the blade 22 between the extended position and the retracted position.

Referring to FIG. 2, the blade 22 is generally arcuate or hook-shaped to define an inner cutting surface 26. As illustrated, the inner cutting surface 26 includes a first surface 28 and a second surface 30. The first and second surfaces 28, 30 angularly extend from each other to define the inner cutting surface 26 having an inverted v-shaped configuration. However, alternate configurations of inner cutting surface 26, such as u-shaped, c-shaped and the like, are easily contemplated by one skilled in the art.

The tubular member 12 also includes a distal tip 32 having a slot 34. As illustrated, the distal tip 32 is generally conical. Further, the distal tip 32 and slot 34 are adapted to receive the blade 22 when the tension member 14 and blade 22 are moved from the extended position to the retracted position. The slot 34 functions as a keyhole to minimize rotation of the blade 22 when moved to the retracted position.

The adjustment mechanism 24 includes a female member 58, a male member 40 and an anchor 42. The anchor 42 is affixed to the proximal end 20 of the tension member 14 and is also affixed to or received within the male member 40. The male member 40 is received within a cavity 44 of the female member 38. Further, an inner surface 46 of the female member 38 defines the cavity 44 and is threaded. An outer surface 48 of the male member 40 is correspondingly threaded. The corresponding threaded surfaces 46, 48 engage and disengage when the male member 40 is received within the cavity 44 of the female member 38. Alternately, the female member 38 may include an insert 49. The insert is received within the cavity 44 and is preferably made of stainless steel. The insert includes the threads defining inner surface 46 and corresponding to the threaded outer surface 48 of the male member 40.

A distal end 50 of the male member 40 includes a handle 52. The handle 52 is used to actuate the adjustment mechanism 24 for movement of the tension member 14 and blade 22 between the extended and retracted positions. Optionally, when the male and female members 38, 40 include corresponding threaded surfaces 46, 48, the adjustment mechanism 14 includes a release mechanism (not shown). The release mechanism disengages the threaded surfaces 46, 48 for actuation of the adjustment mechanism 24 and movement of the tension member 14 and blade 22 to the extended position without having to rotate the male member 40 within the cavity 44 of the female member 38.

Figure 3A:
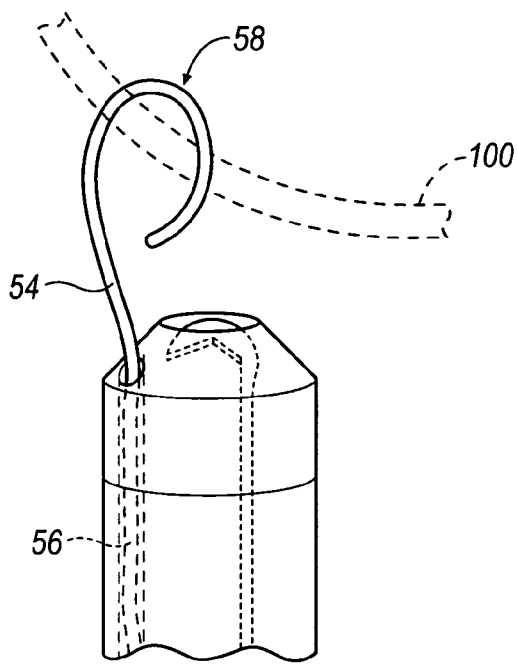
FIGS. 3A-3C illustrate enlarged perspective views of a distal tip of a second embodiment of the endocardial lead cutting apparatus of the present invention.
Figure 3B:
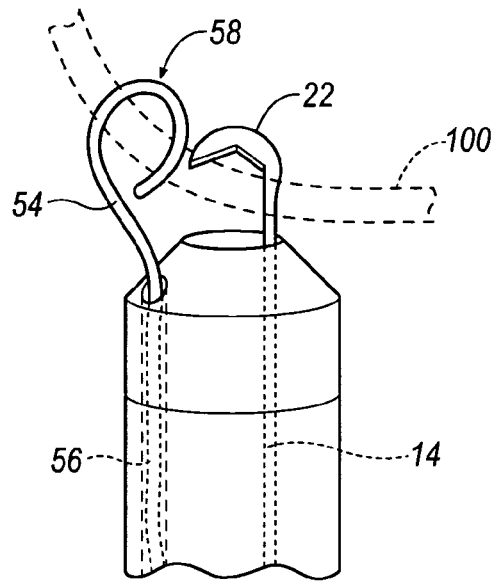
Figure 3C:
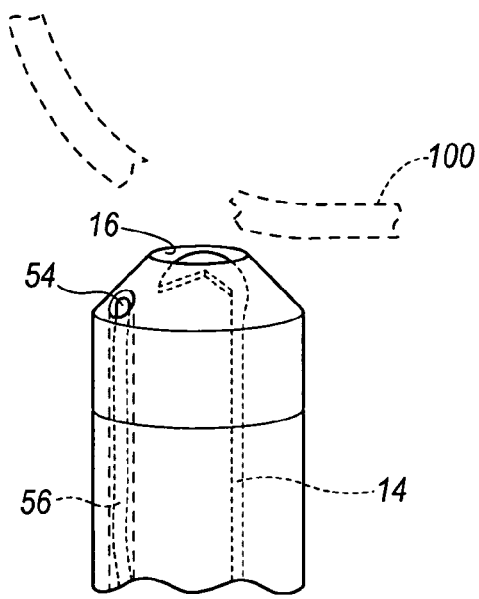

In a second embodiment of the present invention illustrated in FIGS. 3A-3C, the apparatus 10 further includes a capture mechanism 54. The capture mechanism 54 is disposed within the tubular member 12, preferably within a second channel 56. Alternatively, the capture mechanism 54 is received within a second channel 56 disposed upon an outer surface of the tubular member 12. Regardless, the second channel 56 may also include the bearing surface (not shown), such as a coil, to facilitate movement of the capture mechanism 54 between an extended position and a retracted position. The capture mechanism 54 is preferably a deflectable guide wire, made of a flexible or bendable material and having a biased arcuate distal end 58. When retracted within the second channel 56 the biased arcuate distal end 58 is generally longitudinal. In contrast, when extended, the biased arcuate distal end 58 curls to wrap around the endocardial lead 100 (shown in phantom) and draw the lead 100 close to the distal tip 32 of the tubular member 12. A proximal end (not shown) of the capture mechanism 54 extends from the second channel 56 near the proximal end 20 of the tension member 14 and is manually actuated between the extended and retracted positions. Optionally, the proximal end of the capture mechanism 54 may include a handle (not shown) or an adjustment mechanism (also not shown) for facilitating movement between extended and retracted positions.

In operation, the apparatus 10 of FIGS. 1-3 is inserted within a patient's heart (not shown). The capture mechanism 54 is actuated and extended. The biased arcuate distal end 58 of the capture mechanism 54 grasps the endocardial lead 100 by wrapping about the lead 100. The capture mechanism 54 is then actuated and retracted to draw the lead 100 closer to the distal tip 32 of the tubular member 12. Next, the adjustment mechanism 24 is actuated by rotating the male member 40 in a first direction within the cavity 44 of the female member 38 to engage the corresponding threaded surfaces 46, 48. Accordingly, the tension member 14 and blade 22 are extended through the first channel 16 to the extended position outward of the distal tip 32 and slot 34.

Once in the extended position, the generally arcuate or hook-shaped blade 22 extends about the lead 100 such that the inner cutting surface 26 contacts the lead 100. Then, the male member 40 is rotated in an opposite direction within the cavity 44 of the female member 38 to disengage the corresponding threaded surfaces 46, 48. The tension member 14 and blade 22 are moved to the retracted position and the inner cutting surface 26 of the blade 22 cuts through the lead 100. The blade 22 reenters the slot 34 of the distal tip 32 and is retraced within the first channel 16.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the apparatus within the scope of these claims and their equivalents be covered thereby. This description of the invention should be understood to include all novel and non-obvious combinations of elements described herein, and claims may be present in this or a later application to any novel and non-obvious combinations of these elements. The foregoing embodiments are illustrative, and no single feature or element is essential to all possible combination that may be claimed in this or a later application. Where the claims recite "a" or "a first" element of the equivalent thereof, such claims should be understood to include incorporation of one or more such elements, neither requiring nor excluding two or more such elements.

What is claimed, therefore is:

1. An endocardial lead cutting apparatus for cutting a lead implanted within a patient, said apparatus comprising:
 a generally flexible tubular member;
 a tension member disposed within said tubular member and including a distal end and a proximal end;
 at least one blade affixed to said distal end of said tension member;
 an adjustment mechanism adapted to adjust said tension member and said at least one blade between an extended position and a retracted position; and
 wherein said adjustment mechanism includes a female member, a male member and an anchor, said anchor affixed to said proximal end of said tension member and said male member such that insertion and withdrawal of said male member within said female member moves said tension member and said at least one blade between said extended position and said retracted position.

2. The apparatus of claim 1, wherein said generally flexible tubular member includes a first channel for receiving said tension member, said first channel including a bearing surface to facilitate movement of said tension member between said extended position and said retracted position.

3. The apparatus of claim 1, wherein said at least one blade is generally arcuate to define an inner cutting surface.

4. The apparatus of claim 3, wherein said inner cutting surface includes first and second angularly extending surfaces.

5. The apparatus of claim 1, wherein said generally flexible tubular member is reinforced to accommodate applied forces when cutting the lead within the patient.

6. The apparatus of claim 1, wherein said generally flexible tubular member includes a distal tip having a slot adapted to receive said at least one blade when moved from said extended position to said retracted position, said slot being oriented to minimize rotation of said at least one blade.

7. The apparatus of claim 6, wherein said distal tip of said generally flexible tubular member is generally conical.

8. The apparatus of claim 1, wherein said male member and said female member of said adjustment mechanism include corresponding threaded surfaces such that insertion and withdrawal of said male member within said female member includes rotation of said male member such that said corresponding threaded surfaces engage and disengage.

9. The apparatus of claim 8, wherein said female member includes an insert comprising said corresponding threaded surface.

10. The apparatus of claim 1, wherein a proximal end of said male member includes a handle.

11. The apparatus of claim 1, further including a capture mechanism for grasping the lead.

12. The apparatus of claim 11, wherein said capture mechanism is a generally deflectable guide wire.

13. The apparatus of claim 11, wherein said generally flexible tubular member includes a second channel for receiving said capture mechanism.

14. The apparatus of claim 1, wherein said tension member is flexible.

15. The apparatus of claim 1, wherein said generally flexible tubular member is comprised of a radiopaque material.

16. An endocardial lead cutting apparatus for cutting a lead implanted within a patient, said apparatus comprising:
 a generally flexible tubular member having a distal tip;
 a tension member disposed within said tubular member and including a distal end and a proximal end;
 at least one blade affixed to said distal end of said tension member;
 an adjustment mechanism adapted to adjust said tension member and said at least one blade between an extended position and a retracted position; and
 a capture mechanism for grasping the lead;
 wherein said adjustment mechanism includes a female member, a male member and an anchor, said anchor affixed to said proximal end of said tension member and said male member such that insertion and withdrawal of said male member within said female member moves said tension member and said at least one blade between said extended position and said retracted position.

17. The apparatus of claim 16, wherein said capture mechanism is a generally deflectable guide wire.

18. The apparatus of claim 16, wherein said generally flexible tubular member includes a first channel for receiving said tension member and a second channel for receiving said capture mechanism.

19. The apparatus of claim 18, wherein said first and second channels include bearing, surfaces to facilitate movement of said tension member and said capture mechanism.

20. The apparatus of claim 16, wherein said at least one blade is generally arcuate to define an inner cutting surface.

21. The apparatus of claim 2, wherein said inner cutting surface includes first and second angularly extending surfaces.

22. The apparatus of claim 16, wherein a proximal end of said male member includes a handle.

23. The apparatus of claim 16 wherein said male member and said female member of said adjustment mechanism include corresponding threaded surfaces such that insertion and withdrawal of said male member within said female member includes rotation of said male member such that said corresponding threaded surfaces engage and disengage.

24. The apparatus of claim 23, wherein said female member includes an insert comprising said corresponding threaded surface.

25. The apparatus of claim 16, wherein said generally flexible tubular member is reinforced to accommodate applied forces when cutting the lead within the patient.

26. The apparatus of claim 16, wherein said generally flexible tubular member includes a distal tip having a slot adapted to receive said at least one blade when moved from said extended position to said retracted position, said slot being oriented to minimize rotation of said at least one blade.

27. The apparatus of claim 26, wherein said distal tip of said generally flexible tubular member is generally conical.

28. The apparatus of claim 16, wherein said tension member is generally flexible.

29. The apparatus of claim 16, wherein said generally flexible tubular member is comprised of a generally radiopaque material.

30. An endocardial lead cutting apparatus for cutting a lead implanted within a patient, said apparatus comprising:
 a generally flexible tubular member having a distal tip;

a tension member disposed within said tubular member and including a distal end and a proximal end;

at least one blade affixed to said distal end of said tension member;

an adjustment mechanism adapted to adjust said tension member and said at least one blade between an extended position and a retracted position; and a capture mechanism for grasping the lead wherein said generally flexible tubular member includes a distal tip having a slot adapted to receive said at least one blade when moved from said extended position to said retracted position, said slot being oriented to minimize rotation of said at least one blade.

* * * * *

UNITED STATES PATENT AND TRADEMARK OFFICE
CERTIFICATE OF CORRECTION

PATENT NO. : 7,651,503 B1  Page 1 of 1
APPLICATION NO. : 11/259477
DATED : January 26, 2010
INVENTOR(S) : Coe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1127 days.

Signed and Sealed this

Twenty-third Day of November, 2010

David J. Kappos
*Director of the United States Patent and Trademark Office*